United States Patent
Karube et al.

(10) Patent No.: US 9,902,670 B2
(45) Date of Patent: Feb. 27, 2018

(54) PRODUCTION METHOD FOR COMPOSITION CONTAINING 1,2-DICHLORO-3,3,3-TRIFLUOROPROPENE (HCFO-1223XD) AND/OR 1,1,2-TRICHLORO-3,3,3-TRIFLUOROPROPENE (CFO-1213XA)

(71) Applicant: DAIKIN INDUSTRIES, LTD., Osaka (JP)

(72) Inventors: Daisuke Karube, Osaka (JP); Shun Ohkubo, Osaka (JP); Tatsuya Takakuwa, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days.

(21) Appl. No.: 15/307,956

(22) PCT Filed: May 14, 2015

(86) PCT No.: PCT/JP2015/063938
§ 371 (c)(1),
(2) Date: Oct. 31, 2016

(87) PCT Pub. No.: WO2015/174503
PCT Pub. Date: Nov. 19, 2015

(65) Prior Publication Data
US 2017/0057891 A1   Mar. 2, 2017

(30) Foreign Application Priority Data
May 16, 2014 (JP) ................. 2014-102429

(51) Int. Cl.
C07C 17/06 (2006.01)
C07C 21/18 (2006.01)
C07C 17/25 (2006.01)
C07C 17/15 (2006.01)
C07C 19/10 (2006.01)
C07B 61/00 (2006.01)
C07C 17/383 (2006.01)

(52) U.S. Cl.
CPC .............. *C07C 17/06* (2013.01); *C07C 17/15* (2013.01); *C07C 17/25* (2013.01); *C07C 17/383* (2013.01); *C07C 19/10* (2013.01); *C07C 21/18* (2013.01); *C07B 61/00* (2013.01); *Y02P 20/582* (2015.11)

(58) Field of Classification Search
CPC ......... C07C 17/15; C07C 17/25; C07C 19/10; C07C 21/18; C07C 17/06; C07C 17/383
See application file for complete search history.

(56) References Cited
U.S. PATENT DOCUMENTS
2014/0357907 A1   12/2014 Okamoto et al.

FOREIGN PATENT DOCUMENTS

| | | |
|---|---|---|
| JP | 2011-517681 | 6/2011 |
| JP | 2012-524026 | 10/2012 |
| JP | 2013-87187 | 5/2013 |
| JP | 2014-210765 | 11/2014 |
| WO | 2009/125199 | 10/2009 |
| WO | 2010/123154 | 10/2010 |
| WO | 2013/015068 | 1/2013 |
| WO | 2013/111911 | 8/2013 |
| WO | 2013/122790 | 8/2013 |

OTHER PUBLICATIONS

JP 2013-87187, May 2013, machine translation.*
International Search Report dated Aug. 18, 2015 in International (PCT) Application No. PCT/JP2015/063938.
Notification of Reasons for Refusal dated Aug. 5, 2015 in corresponding Japanese Application No. 2015-098780, with English translation.
Notification of Reasons for Refusal dated Mar. 31, 2016 in corresponding Japanese Application No. 2015-098780, with English translation.
Iwanami Physicochemistry Dictionary, 5$^{th}$ edition, Iwanami Shoten, Publishers, "Oxychlorination", p. 184, Apr. 1998, with partial translation.
Haszeldine, "Reactions of Fluorocarbon Radicals. Part V.* Alternative Syntheses for Trifluoroinethylacetylene (3:3:3-Trifluoropropyne), and the Influence of Polyfluorogoups on Adjacent Hydrogen and Halogen Atoms", Journal of Chemical Society, Part IC, 1951, pp. 2495-2504.
Bost et al., "Reactions of Some Highly Chlorinated Unsaturated $C_5$ Hydrocarbons with Chlorine and Copper", Journal of American Chemical Society, vol. 70, Mar. 1948, pp. 1027-1029.
Extended European Search Report dated Aug. 29, 2017 in corresponding European Application No. 15793310.2.

* cited by examiner

*Primary Examiner* — Jafar Parsa
(74) *Attorney, Agent, or Firm* — Wenderoth, Lind & Ponack, L.L.P.

(57) ABSTRACT

The present invention provides a method that produces a composition containing 1223xd and/or 1213xa by a gas-phase reaction, and that achieves production efficiency higher than known methods. The present invention provides a method for producing a composition containing at least one fluorine-containing olefin selected from 1,2-dichloro-3,3,3-trifluoropropene (HCFO-1223xd) and 1,1,2-trichloro-3,3,3-trifluoropropene (CFO-1213xa), the method comprising subjecting at least one starting compound selected from a chlorine-containing alkane represented by Formula (1-1): $CF_3CHXCHX_2$, wherein each X is independently H or Cl, with the proviso that at least one X represents Cl, and a chlorine-containing alkene represented by Formula (1-2): $CF_3CX=CX_2$, wherein each X is independently H or Cl, with the proviso that at least one X represents Cl, to a gas-phase oxychlorination reaction in a temperature range of 380° C. or lower in the presence of oxidative gas and hydrogen chloride gas.

13 Claims, 1 Drawing Sheet

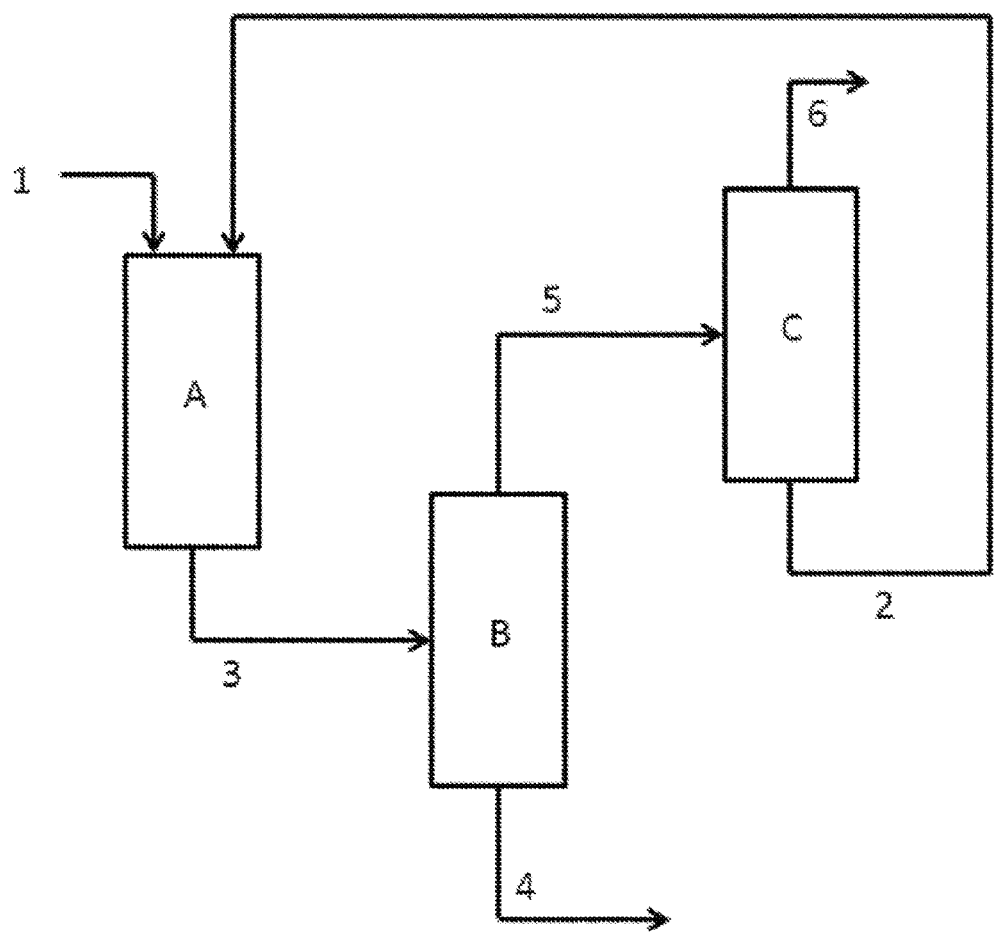

PRODUCTION METHOD FOR COMPOSITION CONTAINING 1,2-DICHLORO-3,3,3-TRIFLUOROPROPENE (HCFO-1223XD) AND/OR 1,1,2-TRICHLORO-3,3,3-TRIFLUOROPROPENE (CFO-1213XA)

TECHNICAL FIELD

The present invention relates to a method for producing a composition containing 1,2-dichloro-3,3,3-trifluoropropene (HCFO-1223xd) and/or 1,1,2-trichloro-3,3,3-trifluoropropene (CFO-1213xa).

BACKGROUND ART

HCFO-1223xd and CFO-1213xa have been widely used as a cleaner or the like, and various production methods have been known. For example, a production method is known comprising performing a fluorination reaction of starting compounds, such as 1,1,2,3-tetrachloropropene (HCO-1230xa) and $CCl_3CCl=CHCl$, using antimony (e.g., Non-patent Literature (NPL) 1). Further, a production method is known comprising performing dehydrochlorination of starting compounds, such as $CF_3CCl_2CH_2Cl$ and $CF_3CHClCHCl_2$, using an alkali (e.g., Non-patent Literature (NPL) 2). However, these production methods that are performed in a liquid phase are batch production methods, which are noted as having unsatisfactory production efficiency.

Other than the above, a method is known in which a chlorine source, such as chlorine gas and hydrogen chloride gas, and an oxidative substance are subjected to a gas-phase reaction with starting compounds, such as 3,3,3-trifluoropropene (HFO-1243zf), 2-chloro-3,3,3-trifluoropropene (HCFO-1233xf), and 1,3,3,3-tetrafluoropropene (HFO-1234ze) (e.g., Patent Literature (PTL) 1). A production method involving a gas-phase reaction is advantageous because it is capable of continuously producing a target product, unlike the liquid-phase reaction described above. However, a production method involving gas-phase reaction generates a large number of undesirable by-products, depending on the reaction conditions. There is thus still room for improvement in terms of production efficiency.

Therefore, the development of a method has been in demand that produces a composition containing HCFO-1223xd and/or CFO-1213xa by a gas-phase reaction and that achieves production efficiency higher than known methods.

CITATION LIST

Patent Literature

PTL 1: WO2009/125199

Non-Patent Literature

NPL 1: Journal of Chemical Society (1951) pp. 2495 and 2503
NPL 2: Journal of American Chemical Society (1948) p. 1027

SUMMARY OF INVENTION

Technical Problem

An object of the present invention is to provide a method that produces a composition containing HCFO-1223xd and/ or CFO-1213xa by a gas-phase reaction, and that achieves production efficiency higher than known methods.

Solution to Problem

The present inventors conducted extensive research to achieve the above object and found that the above object is achieved when a specific chlorine-containing compound used as a starting compound is subjected to a gas-phase oxychlorination reaction under specific conditions. The present invention has thus been accomplished.

More specifically, the present invention relates to a method for producing a composition containing HCFO-1223xd and/or CFO-1213xa.

1. A method for producing a composition containing at least one fluorine-containing olefin selected from 1,2-dichloro-3,3,3-trifluoropropene (HCFO-1223xd) and 1,1,2-trichloro-3,3,3-trfluoropropene (CFO-1213xa),
the method comprising
subjecting at least one starting compound selected from a chlorine-containing alkane represented by Formula (1-1): $CF_3CHXCHX_2$, wherein each X is independently H or Cl, with the proviso that at least one X represents Cl, and a chlorine-containing alkene represented by Formula (1-2): $CF_3CX=CX_2$, wherein each X is independently H or Cl, with the proviso that at least one X represents Cl,
to a gas-phase oxychlorination reaction in a temperature range of 380° C. or lower in the presence of oxidative gas and hydrogen chloride gas.

2. The production method according to item 1, wherein the starting compound is at least one member selected from the group consisting of 2,3-dichloro-1,1,1-trifluoropropane (HCFC-243db), 3,3-dichloro-1,1,1-trifluoropropane (HCFC-243fa), 2-chloro-3,3,3-trifluoropropene (HCFO-1233xf), and 1-chloro-3,3,3-trifluoropropene (HCFO-1233zd).

3. The production method according to item 1, wherein the starting compound is 2-chloro-3,3,3-trifluoropropene (HCFO-1233xf).

4. The production method according to any one of items 1 to 3,
the method comprising
subjecting at least one starting compound precursor selected from a chlorine-containing alkane represented by Formula (2-1): $CY_3CHXCHX_2$, wherein each X is independently H or Cl, with the proviso that at least two X's represent Cl, and each Y is independently F or Cl, and
a chlorine-containing alkene represented by Formula (2-2): $CX_3CX=CX_2$, wherein each X is independently H or Cl, with the proviso that at least two X's represent Cl,
to a gas-phase fluorination reaction using hydrogen fluoride to convert the precursor into the starting compound; and
subjecting the starting compound obtained by the conversion to a gas-phase oxychlorination reaction in a temperature range of 380° C. or lower in the presence of oxidative gas and hydrogen chloride gas to obtain the composition.

5. The production method according to item 4, wherein the starting compound precursor is at least one member selected from the group consisting of
1,1,1,2,3-pentachloropropane (HCC-240db), 1,1,1,3,3-pentachloropropane (HCC-240fa), 1,1,1,3-tetrachloropropane (HCC-250fb), 1,1,2,3-tetrachloro-1-fluoropropane (HCFC-241db), 1,2,3-trichloro-1,1-difluoropropane (HCFC-242dc), 1,1,3,3-tetrachloro-1-fluoropropane (HCFC-241fa), 1,3,3-trichloro-1,1-difluoropropane (HCFC-242fa), 1,1,2,3- tetrachloropropene (HCC-1230xa), 2,3,3,3-tetrachloropropene (HCO-1230xf), and 1,1,3,3-tetrachloropropene (HCO-1230za).

6. The production method according to any one of items 1 to 3,
the method comprising
a step of generating hydrogen chloride gas by subjecting a part of the starting compound to a gas-phase fluorination reaction using hydrogen fluoride, wherein the generated hydrogen chloride gas is used as part or all of the hydrogen chloride gas used in the gas-phase oxychlorination reaction.

7. The production method according to item 4 or 5, wherein part or all of the hydrogen chloride gas used in the gas-phase oxychlorination reaction is hydrogen chloride gas generated when the starting compound precursor is subjected to a gas-phase fluorination reaction using hydrogen fluoride.

8. The production method according to any one of items 1 to 7,
the method comprising
a step of separating a high-boiling-point fraction having a boiling point of 30° C. or higher at atmospheric pressure and containing at least one of HCFO-1223xd and CFO-1213xa from the composition.

9. The production method according to any one of items 1 to 7, the method comprising:
a step of separating a high-boiling-point fraction having a boiling point of 30° C. or higher at atmospheric pressure and containing at least one of HCFO-1223xd and CFO-1213xa from the composition; and
a step of recycling a part or all of compounds from the residue after separation, contain three carbon atoms, and have a boiling point lower than that of HCFC-1223xd, into the gas-phase oxychlorination reaction.

10. The production method according to any one of items 1 to 9, wherein the oxidative gas is at least one of oxygen gas and chlorine gas.

11. The production method according to item 10, wherein the oxidative gas is the oxygen gas, and the oxygen gas is used at the time of the gas-phase oxychlorination reaction in an amount of 3 equivalents or less, relative to total organic substances.

12. The production method according to item 10, wherein the oxidative gas is the chlorine gas, and the chlorine gas is used at the time of the gas-phase oxychlorination reaction in an amount of 0.5 equivalent or less, relative to total organic substances.

13. The production method according to item 10, wherein the oxidative gas is the oxygen gas, and the gas-phase oxychlorination reaction is performed in a temperature range of 300 to 380° C.

14. The production method according to item 10, wherein the oxidative gas is the chlorine gas, and the gas-phase oxychlorination reaction is performed in a temperature range of 150 to 350° C.

15. The production method according to any one of items 1 to 14, wherein the gas-phase oxychlorination reaction is performed using a catalyst containing at least one member selected from the group consisting of chromium, copper, tin, ruthenium, vanadium, niobium, molybdenum, rhodium, antimony, osmium, manganese, cobalt, and platinum.

16. The production method according to item 15, wherein the catalyst is supported on at least one carrier selected from the group consisting of chromia, alumina, zirconia, titania, chromium fluoride, and aluminium fluoride.

Advantageous Effects of Invention

The production method of the present invention, which produces a target composition by a gas-phase reaction, enables the continuous production of a target composition, and in this respect, achieves production efficiency higher than known methods that involve a liquid-phase reaction. Further, the production method of the present invention comprises subjecting a specific chlorine-containing compound used as a starting compound to a gas-phase oxychlorination reaction under specific conditions; thus, the by-products are of the type that are advantageously recycled into the gas-phase oxychlorination reaction, and the production efficiency of the production method of the present invention is higher than that of known methods that involve a gas-phase reaction.

BRIEF DESCRIPTION OF DRAWINGS

FIG. 1 illustrates an embodiment of the substance flow according to the production method (continuous system) of the present invention.

DESCRIPTION OF EMBODIMENTS

The following describes the production method of the present invention in detail.

The method of the present invention comprises producing a composition containing HCFO-1223xd and/or CFO-1213xa. More specifically, the method of the present invention comprises subjecting at least one starting compound selected from a chlorine-containing alkane represented by Formula (1-1): $CF_3CHXCHX_2$, wherein each X is independently H or Cl, with the proviso that at least one X represents Cl, and a chlorine-containing alkene represented by Formula (1-2): $CF_3CX=CX_2$, wherein each X is independently H or Cl, with the proviso that at least one X represents Cl, to a gas-phase oxychlorination reaction in a temperature range of 380° C. or lower in the presence of oxidative gas and hydrogen chloride gas, to produce a composition containing at least one fluorine-containing olefin selected from 1,2-dichloro-3,3,3-trifluoropropene ($CF_3CCl=CHCl$ (HCFO-1223xd)) and 1,1,2-trichloro-3,3,3-trifluoropropene ($CF_3CCl=CCl_2$ (CFO-1213xa)).

The production method of the present invention, which has the above feature, produces a target composition by a gas-phase reaction, enabling the continuous production of a target composition. In this respect, the production method of the present invention achieves production efficiency higher than that of known methods that involve limpid-phase reaction. Further, the production method of the present invention comprises subjecting a specific chlorine-containing compound used as a starting compound to a gas-phase oxychlorination reaction under specific conditions; thus, the by-products are of the type that are advantageously recycled into the gas-phase oxychlorination reaction, and the production efficiency of the production method of the present invention is higher than that of known methods that involve a gas-phase reaction.

As a starting compound, the production method of the present invention uses a chlorine-containing alkane represented by Formula (1-1): $CF_3CHXCHX_2$, wherein each X is independently H or Cl, with the proviso that at least one X represents Cl, and/or a chlorine-containing alkene represented by Formula (1-2): $CF_3CX=CX_2$, wherein each X is independently H or Cl, with the proviso that at least one X represents Cl.

Examples of a chlorine-containing alkane represented by Formula (1-1) include 2,3-dichloro-1,1,1-trifluoropropane (HCFC-243db), and 3,3-dichloro-1,1,1-trifluoropropane (HCFC-243fa).

Examples of a chlorine-containing alkene represented by Formula (1-2) include 2-chloro-3,3,3-trifluoropropene (HCFO-1233xf), and 1-chloro-3,3,3-trifluoropropene (HCFO-1233zd).

Of these starting compounds, HCFO-1233xf is particularly preferable in the present invention. The use of HCFO-1233xf is advantageous because it is easily available, and also because the difference in the boiling point between HCFO-1233xf and a target compound, i.e., HCFO-1223xd or CFO-1213xa, is relatively large.

In the production method of the present invention, the oxidative gas is not limited, and at least one of oxygen gas and chlorine gas is preferably used.

When used as the oxidative gas, oxygen gas is used at the time of gas-phase oxychlorination reaction in an amount of preferably 3 equivalents or less, more preferably 0.05 to 3 equivalents, and most preferably 0.1 to 1 equivalent, relative to the total organic substances. When used as the oxidative gas, chlorine gas is used at the time of gas-phase oxychlorination reaction in an amount of preferably 0.5 equivalent or less, more preferably 0.001 to 0.5 equivalent, and most preferably 0.005 to 0.1 equivalent, relative to the total organic substances. The amount "at the time of . . . reaction" refers to an amount at the time that the reaction is initiated when it is a batch reaction process, and refers to an amount at the inlet of a reactor when it is a continuous reaction process.

Although an overly large amount of oxidative gas improves the yield of the target compound (HCFO-1223xd and/or CFO-1213xa; hereinafter abbreviated as a "target compound"), it also increases the generation of by-products (e.g., a compound whose C—C bond is cleaved, carbon dioxide gas, and a compound whose terminal $CF_3$ is chlorinated) that cannot be converted into the target compound even when recycled into the gas-phase oxychlorination reaction. Thus, the use of an overly large amount of oxidative gas is not preferable. An overly small amount of the oxidative gas may decrease the efficiency of a gas-phase oxychlorination reaction, or the efficiency of a gas-phase fluorination reaction of a starting compound or a starting compound precursor performed to generate hydrogen chloride.

In the production method of the present invention, the amount of hydrogen chloride gas is not limited, and hydrogen chloride gas is used in an amount or preferably 0.1 to 10 equivalents, and more preferably 0.2 to 5 equivalents, relative to the starting compound with which a gas-phase oxychlorination reaction is performed. The amount of hydrogen chloride gas also refers to an amount at the time that the reaction is initiated when it is a batch reaction process, and refers to an amount at the inlet of a reactor when it is a continuous reaction process.

An overly large amount of hydrogen chloride gas is not preferable because it may cause hydrogen chloride-induced side reactions to take place, or cause catalyst degradation to decrease the activity when a catalyst is used together. An overly small amount of hydrogen chloride gas may decrease the efficiency of a gas-phase oxychlorination reaction.

The hydrogen chloride gas may be added as hydrogen chloride gas from outside. Alternatively, hydrogen chloride gas generated in the production method of the present invention may be used.

For example, in one embodiment of the production method of the present invention, the method comprises a step of generating hydrogen chloride gas by subjecting a part of the starting compound to a gas-phase fluorination reaction using hydrogen fluoride, and the generated hydrogen chloride gas is used as part or all of the hydrogen chloride gas used in a gas-phase oxychlorination reaction. In another embodiment of the production method of the present invention, the method comprises a step of subjecting a part of the starting compound (starting compound A) to a gas-phase fluorination reaction using hydrogen fluoride to convert it, while generating hydrogen chloride gas, into either a starting compound B or a low-boiling compound having a boiling point lower than starting compound A, and the generated hydrogen chloride as is used as part or all of the hydrogen chloride gas used in a gas-phase oxychlorination reaction. Starting compound B or the low-boiling compound having boiling point lower than starting compound A produced in the gas-phase fluorination reaction may both be subjected to the gas-phase oxychlorination reaction. In still another embodiment of the present invention, a starting compound precursor is subjected to a gas-phase fluorination reaction using hydrogen fluoride, and hydrogen chloride gas generated when the precursor is converted into a starting compound is used as part or all of the hydrogen chloride gas in a gas-phase oxychlorination reaction.

Specific examples of the starting compound that is subjected to a gas-phase fluorination reaction using hydrogen fluoride to generate hydrogen chloride include HCFO-1233xf, HCFO-1233zd, HCFC-243db, and HCFC-243fa.

The starting compound precursor that is subjected to a gas-phase fluorination reaction using hydrogen fluoride to be converted into the starting compound while hydrogen chloride gas is generated is, for example, at least one starting compound precursor selected from a chlorine-containing alkane represented by Formula (2-1): $CY_3CHXCHX_2$, wherein each X is independently H or Cl, with the proviso that at least two X's represent Cl, and each Y is independently F or Cl, and a chlorine-containing alkene represented by Formula (2-2) $CX_3CX=CX_2$, wherein each X is independently H or Cl, with the proviso that at least two X's represent Cl.

Examples of chlorine-containing alkanes represented by Formula (2-1) include 1,1,1,2,3-pentachloropropane (HCC-240db), 1,1,1,3,3-pentachloropropane (HCC-240fa), 1,1,1,3-tetrachloropropane (HCC-250fb), 1,1,2,3-tetrachloro-1-fluoropropane (HCFC-241db), 1,2,3-trichloro-1,1-difluoropropane (HCFC-242dc), 1,1,3,3-tetrachloro-1-fluoropropane (HCFC-241fa), and 1,3,3-trichloro-1,1-difluoropropane (HCFC-242fa). Of these chlorine-containing alkanes, 1,1,1,2,3-pentachloropropane (HCC-240db), 1,1,1,3,3-pentachloropropane (HCC-240fa), and 1,1,1,3-tetrachloropropane (HCC-250lb) are particularly preferable from the viewpoint of easy availability.

Examples of chlorine-containing alkenes represented by Formula (2-2) include 1,1,2,3-tetrachloropropene (HCO-1230xa), 2,3,3,3-tetrachloropropene (HCO-1230xf), and 1,1,3,3-tetrachloropropene (HCC-1230za). Of these chlorine-containing alkenes, 1,1,2,3-tetrachloropropene (HCO-1230xa) and 1,1,3,3-tetrachloropropene (HCO-1230za) are particularly preferable from the viewpoint of, for example, easy availability and stability.

In the production method of the present invention, not only hydrogen chloride gas generated when the starting compound precursor is subjected to a gas-phase fluorination reaction using hydrogen fluoride, but also the obtained starting compound, may be subjected to the gas-phase oxychlorination reaction performed in the production method of the present invention.

The amount of hydrogen fluoride used to react with the starting compound or the starting compound precursor is not limited, and is preferably 1 to 100 equivalents, and more preferably 1 to 20 equivalents, relative to the starting compound or the starting compound precursor. The amount of hydrogen fluoride used also refers to an amount at the time that the reaction is initiated when it is a batch reaction process, and refers to an amount at the inlet of a reactor when it is a continuous reaction process.

In the production method of the present invention, a gas-phase oxychlorination reaction proceeds in a temperature range of 380° C. or lower in the presence of the starting compound, oxidative gas, and hydrogen chloride gas to produce a composition containing the target compound.

The conditions of the gas-phase oxychlorination reaction are not limited as long as the temperature range is 380° C. or lower, and as long as the target compound is produced. The temperature range is usually set to 150 to 380° C. When, in particular, oxygen gas is used as the oxidative gas, the temperature range is preferably set to 300 to 380° C. (in particular 330 to 380° C.), and when chlorine gas is used as the oxidative gas, the temperature range is preferably set to 150 to 350° C. (in particular 250 to 350° C.). Although an overly high reaction temperature improves the yield of the target compound, it also increases the generation of by-products (e.g., a compound whose C—C bond is cleaved, carbon dioxide gas, and a compound whose terminal $CF_3$ is chlorinated) that cannot be converted into the target compound even when recycled into the gas-phase oxychlorination reaction. Thus, an overly high reaction temperature is not preferable. An overly low reaction temperature may decrease the efficiency of the gas-phase oxychlorination reaction, and in addition, a starting compound (e.g., 243db) that has a boiling point as high as the target compound would remain without being consumed in the reaction, possibly hindering the separation of the target compound from the composition obtained by the reaction.

At the time of gas-phase oxychlorination reaction, it is preferable to use an oxidative catalyst to accelerate the reaction. Examples of catalysts include those that contain a component such as chromium, copper, tin, ruthenium, vanadium, niobium, molybdenum, rhodium, antimony, osmium, manganese, cobalt, and platinum. These components are either oxidative catalysts by themselves or converted into an oxidative catalyst in the presence of oxidative gas to function as a catalyst. These catalysts may be used singly or in a combination of two or more. These catalysts may be supported on at least one carrier, such as chromia, alumina, zirconia, titania, chromium fluoride, and aluminium fluoride.

The pressure during the gas-phase oxychlorination reaction is not particularly limited, and the reaction may be performed under reduced pressure, ordinary pressure, or increased pressure. The reaction is usually carried out at pressure near atmospheric pressure (0.1 MPa). The reaction also proceeds smoothly under reduced pressure of less than 0.1 MPa. It is also possible to carry out the reaction under increased pressure within a range in which the starting material does not liquefy.

Examples of specific embodiments of the method of the present invention include a method comprising optionally placing a catalyst into a tubular flow reactor, and introducing the starting compound, oxidative gas, and hydrogen chloride gas into the reactor.

The starting compound may be in a liquid form when supplied as long as the starting compound is in a gaseous form during the reaction. For example, when the starting compound is liquid at an ordinary temperature and ordinary pressure, the starting compound is vaporized using a vaporizer (vaporization region), passed through a preheating region, and then supplied to a reaction region. In this manner, the reaction is conducted in a gas phase. When a catalyst is used, the reaction may be carried out by supplying the starting compound in a liquid form to a reaction apparatus, heating a catalyst layer placed in the reactor to the vaporization temperature of the starting compound or higher, and vaporizing the starting compound when the compound enters the reaction region.

The reactor is preferably made of a material resistant to the corrosive action of hydrogen fluoride, such as Hastelloy, Inconel, Monel, or the like.

When a catalyst is used, the contact time of the starting compound and the catalyst is not limited; however, an excessively short contact time results in insufficient conversion in the reaction while an excessively long contact time can result in an increased formation of undesirable byproducts. Bearing this in mind, an appropriate contact time may be selected. For example, the contact time, which is represented by $W/F_0$, is preferably adjusted to about 0.5 to 100 g·sec/mL, and more preferably about 1 to 50 g·sec/mL. $W/F_0$ is the ratio of the catalyst amount Wg to the total flow rate $F_0$ (flow rate at 0° C., 0.1 MPa: mL/sec) of the starting material gas supplied to the reaction system.

In the production method of the present invention, it is preferable for the gas-phase oxychlorination reaction to continuously produce the target compound by recycling unreacted starting materials and by-products. Thus, the yield of the target compound in a single gas-phase oxychlorination reaction is preferably 1% or more, and more preferably 2% or more, relative to the starting compound.

Various separation procedures and separation processes are applicable to separation and collection of fractions for recycling; separation and collection of high-boiling-point fractions that have high chlorination degree and contain the target compound; and separation and collection of acid contents or oxidative substance, such as hydrogen chloride, hydrogen fluoride, and chlorine gas.

Examples of a method for separating fractions include a method of fractional distillation or rectification using a distillation column, and a method of extractive distillation using a solvent. Further, an adsorption column or a washing column may be provided to remove, during the separation process, an acid content or oxidative substance used in the reaction. It is also possible to provide a liquid separation tank to remove and collect, an excessively used acid content separated from the organic substance by condensation and liquefaction.

An example of an effective recycling process comprises transferring a reaction mixture collected from the outlet of a reactor to a distillation column, and separating target-compound-containing high-boiling-point fractions with high chlorination degree (in particular, high-boiling-point fractions having a boiling point of 30° C. or higher at atmospheric pressure) while recycling fractions suitable for recycling separated from the remaining low-boiling-point fractions with low chlorination degree. It is also possible to transfer a reaction mixture collected from the outlet of a reactor to a distillation column, first separate low-boiling-point component-containing fractions that are not to be recycled and low-boiling-point fractions that are to be recycled in this order, and then separate target-compound-containing high-boiling-point fractions from the residue after separation.

Low-boiling-point fractions to be recycled are preferably those that can be converted into the target compound when returned to the gas-phase oxychlorination reaction, and those having a larger difference in boiling point, compared to the boiling point of the target compound. Specifically, fractions having a boiling point difference of 10° C. or more, compared to the boiling point of high-boiling-point fractions, i.e., fractions having a boiling point of 20° C. or lower at atmospheric pressure, are preferable. Examples include HCFO-1233xf, HCFO-1233zd, HCFC-244bb, and HCFC-244fa. Low-boiling-point fractions having higher fluorination degree and lower boiling point than those of the starting compound are also preferable to be subjected to the gas-phase oxychlorination reaction again to be recycled. Examples include HFC-245cb, HFO-1234ze, and HFC-245fa. When these low-boiling-point fractions are returned to the gas-phase oxychlorination reaction, the chlorination degree is gradually increased, and the low-boiling-point fractions are eventually converted into the target compound.

In the production method of the present invention, a reaction mixture collected from the outlet of a reactor is transferred to a distillation column, high-boiling-point fractions having a boiling point of 30° C. or higher at atmospheric pressure are separated, and recycling components are collected from the residue after separation. This reduces the generation of overly chlorinated by-products and carbon dioxide gas, as well as by-products whose C—C bond is cleaved, at the time of recycling reaction. Further, h boiling-point fractions have a boiling point higher than ordinary temperature, and thus have a low vapor pressure and require no special apparatus when handling. Therefore, to separate the target compound from these fractions is very easy in terms of cost. HCFO-1223xd has a boiling point of 51° C., and CFO-1213xa has a boiling point of 88° C.

In the production method of the present invention, necessary compounds may be separately extracted from the fluorinated low-boiling-point fractions and used as additional target compounds. For example, HFO-1234yf, HFO-1234ze, and the like may be separately extracted from low-boiling-point fractions and used as additional target compounds. In this case, an example of the separation process comprises transferring a reaction mixture collected from the outlet of a reactor to a distillation column, separating the mixture into (1) low-boiling-point fractions containing hydrogen chloride; compounds, such as HFO-1234yf and HFO-1234ze, which are to be additional target compounds; and gases having a boiling point of about −20° C. or lower, such as oxygen gas and carbon dioxide gas, and (2) high-boiling-point fractions containing a component to be recycled; a target-compound-containing component; and hydrogen fluoride. Subsequently, the high-boiling-point fractions are separated into fractions to be recycled and target-compound-containing fractions to thereby obtain the target compound. The low-boiling-point fractions are transferred to another distillation column, and separated into fractions having the lowest boiling point and containing non-condensable gas having a boiling point of about −30° C. or lower, such as oxygen gas and carbon dioxide gas, and low-boiling compounds that are to be additional target compounds, such as HFO-1234yf and HFO-1234ze. The use of such a process enables separation and production of both the target compound and additional target compounds, such as HFO-1234yf and HFO-1234ze.

EXAMPLES

The present invention is described in more detail below with reference to Examples and Comparative Examples but is not limited to these.

Example 1

A chromium oxide ($Cr_2O_3$) catalyst (10.5 g) used as a catalyst was placed in a tubular Hastelloy reactor having a length of 1 m.

The reactor was heated, and nitrogen gas and hydrogen fluoride gas were first introduced to fluorinate the catalyst. The heating temperature and introduction rate were performed in a stepwise manner shown in the following two steps so as to avoid, for example, catalyst deterioration due to the rapid reaction of the catalyst and hydrogen fluoride. Step 1: at 200° C.; nitrogen gas: 450 Nml/min (the flow rate at 0° C. and 0.1 MPa; the same applies hereinafter); hydrogen fluoride gas: 50 Nml/min; 1 hour.
Step 2: at 330'C; nitrogen gas: 100 Nml/min; hydrogen fluoride gas: 400 Nml/min; 1 hour.

The flow rates of nitrogen gas and hydrogen fluoride gas, and the temperature, were changed over a period of 1.5 hours between step 1 and step 2.

Subsequently, the temperature of the reaction tube was increased to 300° C., which was a reaction temperature, anhydrous hydrogen fluoride gas and chlorine gas were supplied to the reactor at flow rates of 120.0 Nml/min and 0.06 Nml/min, respectively, and the resulting product was maintained for 0.5 hour. Thereafter, a gas of $CCl_3CHClCH_2Cl$ (HCC-240db) was supplied as a starting compound precursor at a flow rate of 6.0 Nml/min. The total flow rate $F_0$ was 126.06 Nml/min, and the contact time $W/F_0$ represented by the amount W of catalyst placed and $F_0$ was 5 g/Nml·sec. The molar equivalent ratio of the anhydrous hydrogen fluoride gas to the starting material supplied was 20, and the molar equivalent ratio of the chlorine gas to the starting material supplied was 0.01.

About 30 hours later, effluent gas from the reactor was analyzed using gas chromatography (GC), and the following were calculated based on the area of gas chromatography: the starting material conversion ratio; the selectivity of 1223xd; the total selectivity of 1234yf, 245cb, and 1234ze as reaction products having a boiling point of 0° C. or lower; the total selectivity of 244bb and 1233zd as reaction products having a boiling point of 0 to 20° C.; the selectivity of 1233xf; and the selectivity of non-recyclable decomposition product.

Table 2 shows the results.

Example 2

As a catalyst, a chromium oxide $Cr_2O_3$ catalyst (10.0 g) containing vanadium oxide $V_2O_5$ in an amount of 20 mol % at a metal atom ratio was placed in a tubular Hastelloy reactor having a length of 1 m.

The catalyst was fluorinated as in the method of Example 1. Thereafter, the temperature of the reaction tube was increased to 350° C., which is a reaction temperature, anhydrous hydrogen fluoride gas and oxygen gas were supplied to the reactor at flow rates of 60.0 Nml/min and 0.6 Nml/min, respectively, and the resulting product was maintained for 0.5 hour. Thereafter, a as of $CF_3CCl=CH_2$ (HCFO-1233xf) was supplied as a starting material at a flow rate of 6.0 Nml/min. The total flow rate $F_0$ was 66.6 Nml/min, and the contact time $W/F_0$ was 9 g/Nml·sec. The molar equivalent ratio of the anhydrous hydrogen fluoride gas to the starting material supplied was 10, and the molar equivalent ratio of the oxygen gas to the starting material supplied was 0.10.

About 30 hours later, effluent gas from the reactor was analyzed as in Example 1, and the following were calculated, based on the area of gas chromatography: the starting material conversion ratio; the selectivity of 1223xd; the total selectivity of 1234yf, 245cb, and 1234ze as reaction products having a boiling point of 0° C. or lower; the total selectivity of 244bb and 1233zd as reaction products having a boiling point of 0 to 20° C.; and the selectivity of non-recyclable decomposition product. Table 2 shows the results.

Example 3

A reaction was performed as in Example 2, except that a chromium oxide $Cr_2O_3$ catalyst containing ruthenium oxide $RuO_2$ was used in an amount of 5 mol % at a metal atom ratio as the catalyst. Table 2 shows the results.

Example 4

A reaction was performed as in Example 2, except that a chromium oxide $Cr_2O_3$ catalyst (50.0 g) containing copper oxide CuO was used in an amount of 20 mol % at a metal atom ratio as the catalyst. Table 2 shows the results.

Example 5

A reaction was performed as in Example 2, using 1233xf as a starting material. However, a chromium oxide $Cr_{23}$ catalyst was used as the catalyst, the reaction temperature was adjusted to 300° C., the HF supply amount was adjusted to 57.75 Nml/min, the HCFC-1233xf supply amount was adjusted to 8.25 Nml/min, and the molar equivalent ratio of the HF supplied to the starting material was adjusted to 7. Then, chlorine gas was supplied at 0.06 Nml/min in place of oxygen gas. Table 2 shows the results.

Example 6

A reaction was performed as in Example 2, except that a chromium oxide $Cr_2O_3$ catalyst containing pentavalent molybdenum oxide in an amount of 10 mol % at a metal atom ratio was used as the catalyst. Table 2 shows the results.

Example 7

Example in which Outlet Gas in Example 2 was Recycled

Table 1 shows the composition (GC %) at each place when recycling was performed.

TABLE 1

| Place | Supply 1 | Recycling supply 2 | Reactor outlet 3 | Distillation column High boiling 4 | Distillation column Low boiling 5 | Separation column Low boiling 6 |
|---|---|---|---|---|---|---|
| 1223xd | — | 0 | 3 | 94 | 0 | 0 |
| 1213xa | — | 0 | 0 | 0 | 0 | 0 |
| 1233xf | 100 | 88 | 70 | 0 | 71 | 0 |
| 1233zd | — | 1 | <1 | 0 | 1 | 0 |
| 1234yf | — | 4 | 13 | 0 | 14 | 53 |
| 1234ze | — | 2 | 2 | 0 | 2 | 3 |
| 245cb | — | 4 | 4 | 0 | 4 | 4 |
| $CO_2$ | — | 0 | 6 | 0 | 6 | 35 |
| Others | — | 1 | 2 | 6 | 2 | 5 |

Comparative Example 1

Example in which Reaction of 1233xf was Performed Using $Cr_2O_3$ Catalyst without Using Oxygen The reaction evaluation was performed as in Example 2, except that a chromium oxide $Cr_2O_3$ catalyst was used as a catalyst, and oxidative gas was not supplied. Table 2 shows the results.

Comparative Example 2

Example in which Cr Catalyst Containing V Was Used, and the Reaction Temperature was Increased to Increase 1223xd The reaction evaluation was performed as in Example 2, except that the amount of catalyst was increased to 22.2 g, and the reaction temperature was changed to 400° C., to increase the production amount of 1223xd. Table 2 shows the results.

TABLE 2

| | Ex 1 | Ex 2 | Ex 3 | Ex 4 | Ex 5 | Ex 6 | Comp. Ex. 1 | Comp. Ex. 2 |
|---|---|---|---|---|---|---|---|---|
| Catalyst | Cr | V—Cr | Ru—Cr | Cu—Cr | Cr | Mo—Cr | Cr | V—Cr |
| Starting material | 240db | 1233xf | 1233xf | 1233xf | 1233xf | 1233xf | 1233xf | 1233xf |
| Oxidative gas | Chlorine | Oxygen | Oxygen | Oxygen | Chlorine | Oxygen | None | Oxygen |
| Hydrogen chloride | Generated within system | Generated within system | Generated within system | Generated within system | Generated within system | Generated within system | Generated within system | Generated within system |
| HF/starting material | 20 | 10 | 10 | 10 | 7 | 10 | 10 | 10 |
| Oxidative gas amount/starting material | 0.01 | 0.10 | 0.10 | 0.10 | 0.01 | 0.10 | 0 | 0.10 |
| Contact time $W/F_0$ | 5 | 20 | 9 | 45 | 20 | 9 | 9 | 20 |
| Reaction time ° C. | 300 | 350 | 350 | 350 | 300 | 350 | 350 | 400 |
| Conversion ratio GC % | 100 | 30 | 10 | 20 | 7 | 19 | 10 | 60 |
| 1223xd Selectivity GC % | 7.8 | 8 | 3.4 | 12 | 15 | 4 | 0.04 | 15 |

TABLE 2-continued

|  | Ex 1 | Ex 2 | Ex 3 | Ex 4 | Ex 5 | Ex 6 | Comp. Ex. 1 | Comp. Ex. 2 |
|---|---|---|---|---|---|---|---|---|
| 1234yf + 245cb + 1234ze selectivity GC % | 1 | 65 | 60 | 64 | 48 | 75 | 97 | 15 |
| 1233zd + 244bb selectivity GC % | 3 | 1 | 8 | 1 | 11 | 4 | 2 | 5 |
| 1233xf selectivity GC % | 83 | — | — | — | — | — | — | — |
| Non-recyclable by-product selectivity GC % | 0 | 26 | 20 | 2 | 0.5 | 13 | 0 | 65 |

In Table 2, the "HF/starting material" represents a molar ratio of HF to the starting material fed to the reactor, and the "oxidative gas amount/starting material" represents a molar ratio of oxidation gas to the starting material fed to the reactor. The unit of contact time $W/F_0$ is g/Nml·sec.

In the production method of the present invention, a mechanism in which the target compound is obtained by subjecting a starting compound to a gas-phase oxychlorination reaction is assumed to be equal to, for example, a mechanism in which hydrogen on the carbon in the starting compound is replaced with Cl by a substitution reaction involving chlorine radicals, and further to a mechanism in which, when the starting compound is an olefin compound, $Cl_2$ is added to the double bond of an olefin compound to once give a saturated compound, and then HCL is removed, resulting in substitution with Cl. The production method of the present invention is capable of producing CFO-1213xa, which suggests that the production method of the present invention is capable of producing, based on the same mechanism, other target compounds, such as HCFO-1223xd or $CF_3CH=CCl_2$ (HCFO-1223za), which is the intermediate thereof.

EXPLANATION OF REFERENCE NUMERALS

A. Reactor
B. Distillation column
C. Low-boiling-point separation column
1. Supply of starting compound etc.
2. Recycling
3. Reactor outlet
4. Distillation column outlet (separation of high-boiling-point fractions)
5. Distillation column outlet (separation of low-boiling-point fractions)
6. Separation column outlet (separation of low-boiling-point fractions)

The invention claimed is:

1. A method for producing a composition containing at least one fluorine-containing olefin selected from 1,2-dichloro-3,3,3-trifluoropropene (HCFO-1223xd) and 1,1,2-trichloro-3,3,3-trifluoropropene (CFO-1213xa),
    the method comprising
    subjecting at least one starting compound selected from a chlorine-containing alkane of the following Formula (1-1): $CF_3CHXCHX_2$, wherein each X is independently H or Cl, with the proviso that at least one X represents Cl, and a chlorine-containing alkene of the following Formula (1-2): $CF_3CX=CX_2$, wherein each X is independently H or Cl, with the proviso that at least one X represents Cl,
    to a gas-phase oxychlorination reaction in a temperature range of 380° C. or lower in the presence of oxygen gas and hydrogen chloride gas.

2. The production method according to claim 1, wherein the starting compound is at least one member selected from the group consisting of 2,3-dichloro-1,1,1-trifluoropropane (HCFC-243 db), 3,3-dichloro-1,1,1-trifluoropropane (HCFC-243fa), 2-chloro-3,3,3-trifluoropropene (HCFO-1233xf), and 1-chloro-3,3,3-trifluoropropene (HCFO-1233zd).

3. The production method according to claim 1, wherein the starting compound is 2-chloro-3,3,3-trifluoropropene (HCFO-1233xf).

4. The production method according to claim 1,
    the method comprising
    subjecting at least one starting compound precursor selected from a chlorine-containing alkane of the following Formula (2-1): $CY_3CHXCHX_2$, wherein each X is independently H or Cl, with the proviso that at least two X's represent Cl, and each Y is independently F or Cl, and
    a chlorine-containing alkene of the following Formula (2-2): $CX_3CX=CX_2$, wherein each X is independently H or Cl, with the proviso that at least two X's represent Cl, to a gas-phase fluorination reaction using hydrogen fluoride to convert the precursor into the starting compound; and
    subjecting the starting compound obtained by the conversion to a gas-phase oxychlorination reaction in a temperature range of 380° C. or lower in the presence of oxygen gas and hydrogen chloride gas to obtain the composition.

5. The production method according to claim 4, wherein the starting compound precursor is at least one member selected from the group consisting of 1,1,1,3,3-pentachloropropane (HCC-240fa), 1,1,1,3-tetrachloropropane (HCC-250fb), 1,1,2,3-tetrachloro-1-fluoropropane (HCFC-241db), 1,2,3-trichloro-1,1-difluoropropane (HCFC-242dc), 1,1,3,3-tetrachloro-1-fluoropropane (HCFC-241fa), 1,3,3-trichloro-1,1-difluoropropane (HCFC-242fa), 1,1,2,3-tetrachloropropene (HCO-1230xa), 2,3,3,3-tetrachloropropene (HCO-1230xf), and 1,1,3,3-tetrachloropropene (HCO-1230za).

6. The production method according to claim 1,
    the method comprising
    a step of generating hydrogen chloride gas by subjecting a part of the starting compound to a gas-phase fluorination reaction using hydrogen fluoride,
    wherein the generated hydrogen chloride gas is used as part or all of the hydrogen chloride gas used in the gas-phase oxychlorination reaction.

7. The production method according to claim 4, wherein part or all of the hydrogen chloride gas used in the gas-phase oxychlorination reaction is hydrogen chloride gas generated when the starting compound precursor is subjected to a gas-phase fluorination reaction using hydrogen fluoride.

8. The production method according to claim 1,
the method comprising
a step of separating a high-boiling-point fraction having a boiling point of 30° C. or higher at atmospheric pressure and containing at least one of HCFO-1223xd and CFO-1213xa from the composition.

9. The production method according to claim 1, the method comprising:
a step of separating a high-boiling-point fraction having a boiling point of 30° C. or higher at atmospheric pressure and containing at least one of HCFO-1223xd and CFO-1213xa from the composition; and
a step of recycling a part or all of compounds from the residue after separation, contain three carbon atoms, and have a boiling point lower than that of HCFO-1223xd, into the gas-phase oxychlorination reaction.

10. The production method according to claim 1, wherein the oxygen gas is used at the time of the gas-phase oxychlorination reaction in an amount of 3equivalents or less, relative to total organic substances.

11. The production method according to claim 1, wherein the gas-phase oxychlorination reaction is performed in a temperature range of 300 to 380° C.

12. The production method according to claim 1, wherein the gas-phase oxychlorination reaction is performed using a catalyst containing at least one member selected from the group consisting of chromium, copper, tin, ruthenium, vanadium, niobium, molybdenum, rhodium, antimony, osmium, manganese, cobalt, and platinum.

13. The production method according to claim 12, wherein the catalyst is supported on at least one carrier selected from the group consisting of chromia, alumina, zirconia, titania, chromium fluoride, and aluminium fluoride.

* * * * *